United States Patent

Heffelfinger et al.

[11] Patent Number: 5,951,838
[45] Date of Patent: Sep. 14, 1999

[54] METHOD AND APPARATUS FOR CORRECTING ILLUMINATION NON-UNIFORMITIES

[75] Inventors: David M. Heffelfinger, San Pablo; Craig Van Horn, Sebastapol, both of Calif.

[73] Assignee: Bio-Rad Laboratories, Inc., Hercules, Calif.

[21] Appl. No.: 08/814,126

[22] Filed: Mar. 10, 1997

[51] Int. Cl.⁶ .................. G01N 27/26; G01N 27/447; G01N 21/25; G01J 7/58
[52] U.S. Cl. .................. 204/461; 204/466; 204/612; 204/616; 356/317; 356/344; 356/417; 250/458.1; 250/459.1; 250/461.1
[58] Field of Search .................. 204/466, 467, 204/468, 469, 470, 616, 617, 618, 619, 620, 621, 612, 606, 461; 356/344, 444, 443, 417, 317; 250/458.1, 459.1, 461.1, 461.2

[56] References Cited

U.S. PATENT DOCUMENTS

| | | | |
|---|---|---|---|
| 3,432,414 | 3/1969 | Rand | 204/461 |
| 4,781,464 | 11/1988 | Allington et al. | 356/444 X |
| 4,832,815 | 5/1989 | Kambara et al. | 204/612 |
| 4,874,492 | 10/1989 | Mackay | 204/612 X |
| 5,104,512 | 4/1992 | Gombocz et al. | 204/616 |
| 5,324,401 | 6/1994 | Yueng et al. | 204/452 |
| 5,459,325 | 10/1995 | Hueton et al. | 356/317 X |

*Primary Examiner*—William H. Beisner
*Assistant Examiner*—John S. Starsiak, Jr.
*Attorney, Agent, or Firm*—David G. Beck; Townsend and Townsend and Crew LLP

[57] ABSTRACT

A method and apparatus for achieving uniform illumination in an electrophoresis apparatus is provided. Uniform illumination allows quantitative measurements of an electrophoresis gel to be made, thus increasing the information which can be obtained from an electrophoretic analysis. Uniform illumination is achieved by scanning the light source, preferably in a trans-illumination mode, across the sample gel in a direction perpendicular to the axis of the source. The light source is comprised of one or more light bulbs placed in a light tray. Variations in light intensity near the source end portions may be minimized using a variety of techniques including extended light bulbs, filters, reflectors, diffusers, or supplemental sources.

13 Claims, 5 Drawing Sheets

METHOD AND APPARATUS FOR CORRECTING ILLUMINATION NON-UNIFORMITIES

The present invention relates generally to electrophoresis reading systems and, more particularly, to a method an d apparatus for removing illumination non-uniformities within an electrophoresis system.

BACKGROUND OF THE INVENTION

In the biotechnical field, fluorescent dyes are routinely used as sensitive, non-isotopic labels. These labels are used to identify and locate a variety of cell structures, ranging from malignant tumors to specific chromosomes in a DNA sequence. A variety of devices have been designed to read fluorescent-labeled samples.

Gel electrophoresis is one technique commonly used in conjunction with fluorescent dyes and other markers to identify specific molecules as well as other tagged units. In this technique an electric field is used to cause the migration of the tagged units through a gel or other solution.

In U.S. Pat. No. 4,874,492 a gel electrophoresis system is disclosed in which samples are treated with fluorescent markers prior to applying them to an electrophoretic gel. The gel is illuminated with a UV source and the fluorescence pattern is detected with a cooled charge-coupled-device (CCD) two-dimensional detector array. The CCD array is cooled to at least −25 degrees C. in order to improve light sensitivity and increase the dynamic range.

In U.S. Pat. No. 5,162,654 a system is disclosed to optically determine which of four fluorophores is fluorescing in an eletrophoresis gel. Fluorescence emitted by the gel passes first through four separate band pass filters and then through four wedge prisms. As a result of this optical configuration, the emitted fluorescence is imaged on four discrete areas on the detector array. The specific fluorophore exited by the irradiation source is determined by comparing the relative intensities of the fluorescence detected in the four detection areas.

In U.S. Pat. No. 5,294,323 the disclosed gel electrophoresis system utilizes a vertical electrophoresis plate. A laser beam passes horizontally through the gel in a direction perpendicular to the longitudinal axis of the electrophoresis plate. The emitted fluorescence is reflected to a solid state imaging sensor such that the reflected pattern is parallel to the direction of the laser beam.

In U.S. Pat. No. 5,324,401 a fluorescence detection system for capillary electrophoresis is disclosed which provides for the simultaneous excitation and detection of fluorescent probes within a plurality of capillaries. The excitation source is a laser which is coupled to the capillaries through an optical fiber bundle. The fluorescence from the capillary array is focussed through a lens and imaged onto a CCD camera for analysis.

In a paper by Sutherland et al. entitled "Electronic Imaging System for Direct and Rapid Quantitation of Fluorescence from Electrophoretic Gels: Application to Ethidium Bromide-Stained DNA" published in *Analytical Biochemistry* 163, 446–457 (1987), the authors describe an imaging system which uses a CCD camera. The CCD camera quantifies the fluorescence received from electrophoretic gels, chromatograms, and other sources. The paper describes several sources of non-uniformities which impact the ability of the system to obtain accurate results.

From the foregoing, it is apparent that an improved electrophoresis apparatus is desired which enables accurate quantitative measurements of fluorescence to be made.

SUMMARY OF THE INVENTION

The present invention provides a method and apparatus for achieving uniform illumination in an electrophoresis apparatus. Uniform illumination permits quantitative measurements of an electrophoresis gel to be made, thus increasing the information which can be obtained from the electrophoretic analysis.

Uniform illumination is achieved by scanning the light source, preferably in a trans-illumination mode, across the sample gel in a direction perpendicular to the axis of the source. Preferably the light source is long enough to prevent variations in source uniformity near the source end portions from affecting the irradiation pattern at the sample. The source is comprised of one or more light bulbs placed in a bulb mounting tray. In a multiple bulb configuration each bulb may be provided with a different intensity profile in order to achieve the desired overall intensity pattern. Filters may also be used in conjunction with the bulbs, either on an individual basis or in total, in order to control the source output. The filters can be used to control both the wavelength and the intensity profiles of the individual bulbs.

In an alternate embodiment of the invention, additional sources are located near the sample. The additional sources are stationary and are designed to reduce variations in the irradiation pattern due to any localized intensity loss exhibited at the source end portions.

A further understanding of the nature and advantages of the present invention may be realized by reference to the remaining portions of the specification and the drawings.

DESCRIPTION OF THE PREFERRED EMBODIMENT

Figure 1:
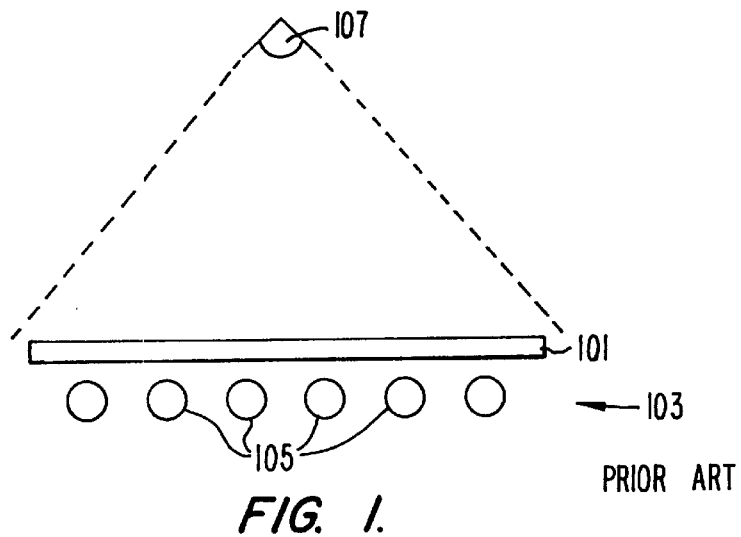
FIG. 1 is an illustration of a cross-section of a gel electrophoresis apparatus according to the prior art.

FIG. 1 is an illustration of a cross-section of a gel electrophoresis apparatus according to the prior art. In this system a gel plate 101 is illuminated by a light source 103. Light source 103 is comprised of a plurality of individual light bulbs 105. The light from source 103 causes fluorophores or other fluorescing material contained within specific areas of sample 101 to fluoresce. A detector 107 receives the fluorescence from sample 101 and uses this information to determine the areas of fluorescence on sample 101.

The light intensity from an individual light bulb 105 is relatively uniform along the majority of the length of the bulb. At either end of the bulb the brightness level exhibits a minor fall-off in intensity. This fall-off can be minimized through the use of reflectors, masks, diffusion filters, or some combination thereof.

Figure 2:
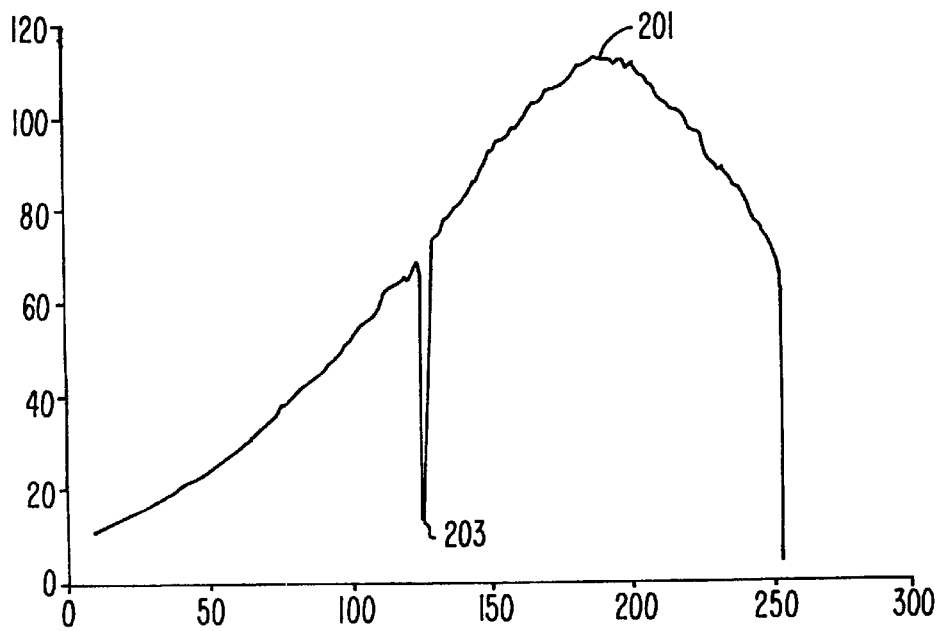
FIG. 2 is the intensity profile of a single light bulb measured perpendicular to the axis of the bulb.
Figure 3:
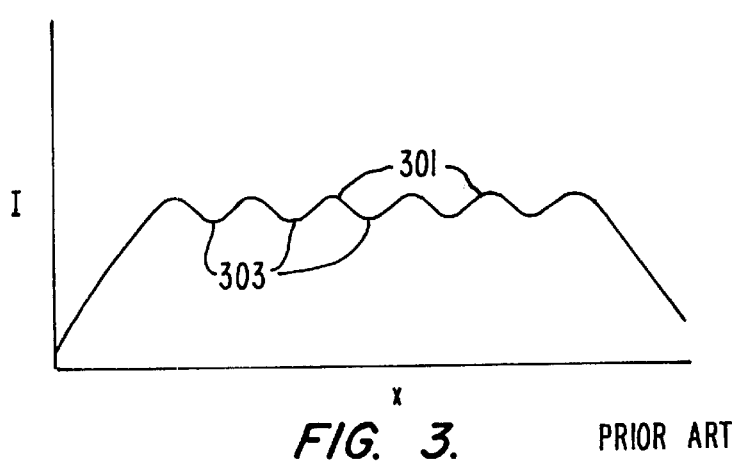
FIG. 3 is an illustration of an intensity profile for source with multiple bulbs.

FIG. 2 is the intensity profile of a single light bulb 105 measured perpendicular to the axis of the bulb. As expected, the profile exhibits a peak 201 centered directly above the bulb with a rapid fall off in the intensity as the distance from the bulb is increased. A dip 203 is a result of a scribe mark on the stage. FIG. 3 is an illustration of an intensity profile for source 103 measured perpendicular to the axes of bulbs 105. Peaks 301 are located over the center lines of the individual bulbs 105 while valleys 303 represent the midpoints between bulbs. Further improvement in source uniformity can be achieved by increasing the number of bulbs and decreasing the separation between bulbs.

Figure 4:
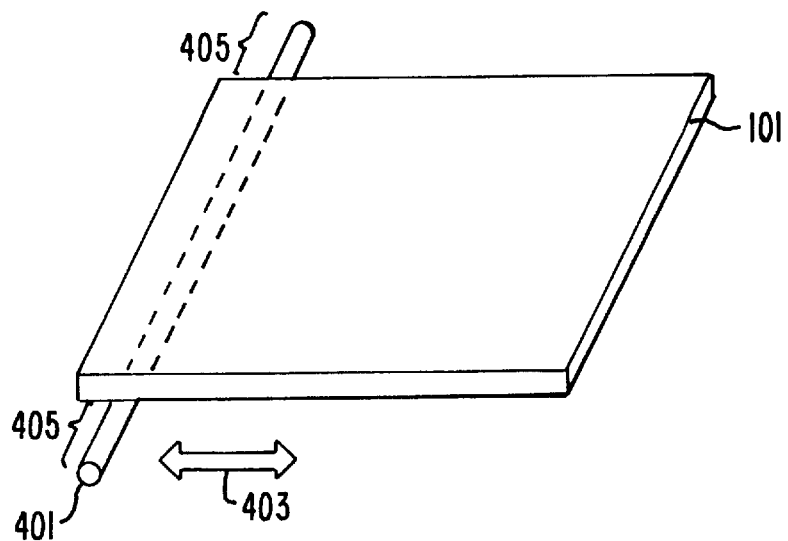
FIG. 4 is an illustration of an embodiment of the invention utilizing a single scanning bulb.

FIG. 4 is an illustration of an embodiment of the invention. Sample 101 is illuminated with a single bulb 401. Bulb 401 is scanned in a direction 403 perpendicular to the axis of bulb 401. Bulb 401 exhibits a high degree of intensity uniformity along the central portion of the bulb axis. There is a minor fall-off in intensity near either end of the bulb. The effects of fall-off can be minimized by extending bulb 401 past the edges of sample 101 by a distance 405. Thus only the central, uniform region of bulb 401 is used to illuminate sample 101. Since bulb 401 is scanned in a direction perpendicular to the region of uniformity, sample 101 will be uniformly illuminated as long as the scanning rate remains constant.

Figure 5:
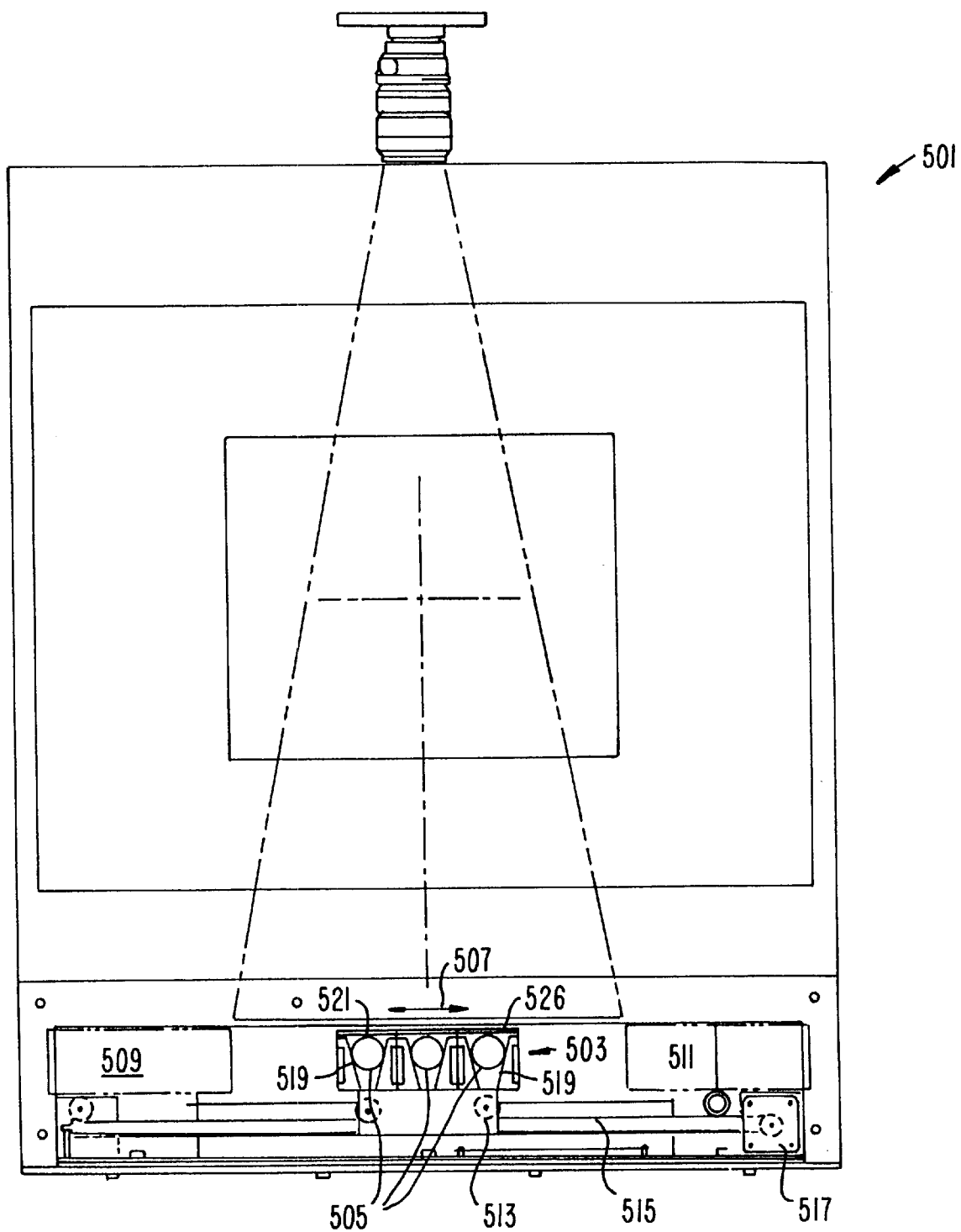
FIG. 5 is a detailed illustration of a crosssectional view of an electrophoresis apparatus according to the present invention.

FIG. 5 is a detailed illustration of a cross-sectional view of an electrophoresis apparatus 501 according to the present invention. In this embodiment a tray 503 containing three bulbs 505 is swept along an axis 507. Preferably light tray 503 is in a location 509 prior to illuminating a sample stage 510. After completing the scan, light tray 503 preferably is placed in a location 511. Locations 509 and 511 lie outside sample stage 510, thus insuring that all areas of a sample (not shown) placed on stage 510 are illuminated by the same intensity profile during the scanning procedure.

Stage 503 has a set of rollers 513 and a pulley belt 515 to permit the necessary scanning motion. Pulley belt 515 is coupled to a motor 517. Motor 517 controls the illumination scan rate.

On either side of each bulb 505 within light tray 503 is a mounting bracket 519. Brackets 519 can be designed to serve multiple purposes besides simply providing a mounting bracket for the bulbs. For example, brackets 519 may be used to control the illumination pattern exiting tray 503. Brackets 519 may also be made of a variety of materials with varying reflectivity and absorption characteristics thus providing further control of the illumination pattern. Additional control of the illumination source is provided by one or more filters 521 residing directly above bulbs 505. Filters 521 may be used to control the wavelengths of the light irradiating the sample. For example, filters 521 may be designed to pass the wavelengths necessary to excite the fluorescent material within the sample while absorbing or reflecting those wavelengths which are the same as those emitted by the sample. Filters 521 can also be designed to diffuse the light emitted by bulbs 505 as well as control the intensity pattern of the emitted light. In addition, the intensity pattern emanating from light tray 503 may be further controlled by individually regulating the excitation energy, the gas mixture, or the gas pressure of bulbs 505.

Figure 6:
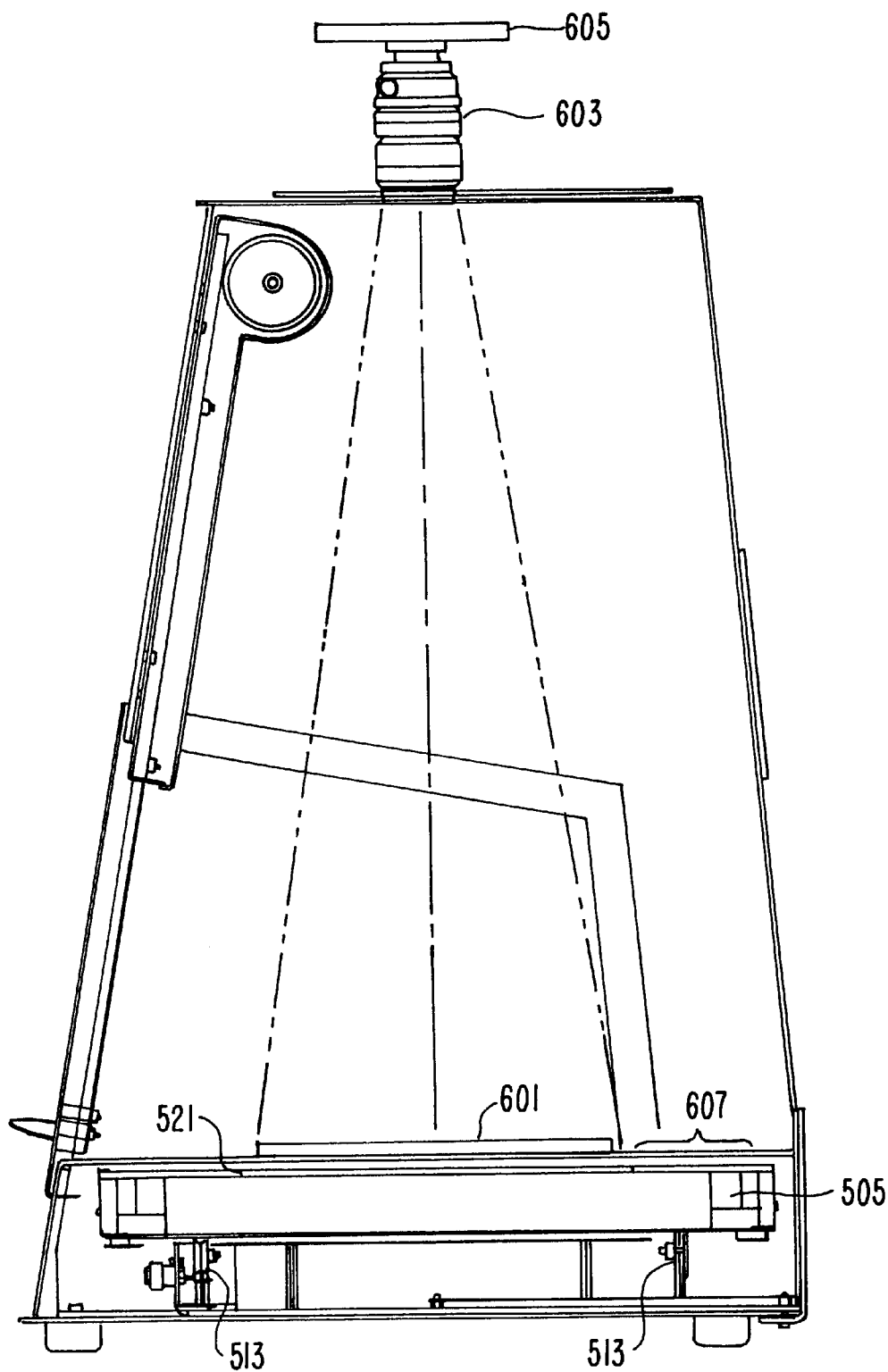
FIG. 6 is an illustration of another view of the embodiment of the apparatus shown in FIG. 5.

FIG. 6 is an illustration of another view of the embodiment of the apparatus shown in FIG. 5. Light from bulb 505 passes through filter 521 and irradiates a sample 601. Since the radiation illuminating any portion of the sample stage is integrated from different parts of bulb(s) 505, spot defects in either the bulb envelope or the filter have minimal effect on the illumination uniformity. The emissions from sample 601 are imaged by a lens assembly 603 onto a detector plane 605. In the preferred embodiment detector 605 is a two-dimensional CCD array.

A portion 607 of bulbs 505 extend beyond the borders of sample 601. Since the light intensity drops off near the ends of the bulbs, the additional bulb length insures that the light illuminating the sample is uniform along a direction parallel to the axis of bulbs.

Figure 7:
FIG. 7 is a cross-section of an alternate embodiment of the invention utilizing one or more light sources in addition to the scanning light source.
Figure 7:
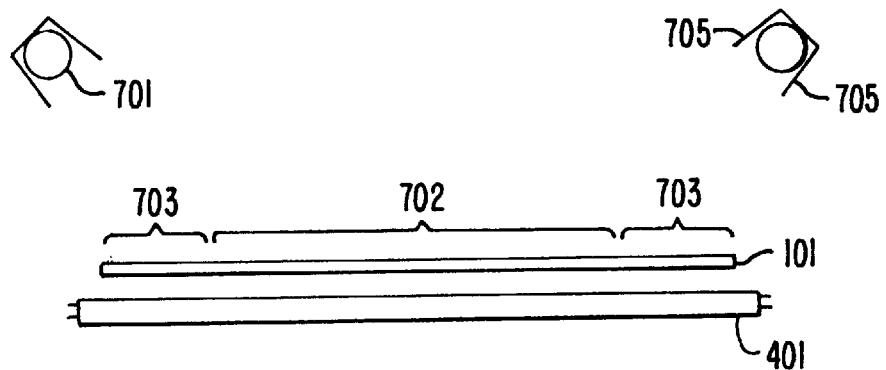

FIG. 7 is a cross-section of an alternate embodiment of the invention. As in the previous embodiment, bulb 401 is scanned in a direction perpendicular to the axis of the bulb. This embodiment also includes additional light sources 701. Sources 701 can be used to offset the lower light intensities irradiating edge portions 703 of sample 101 from bulb 401. Although this edge effect may be a function of non-uniformities in the emission of bulb 401, it may also arise from the illumination geometry. Specifically, the central portion 702 of sample 101 receives light from both sides while portions 703 receive light from the same length of bulb, but from a much greater distance. The degree to which this effect controls the uniformity depends upon the distance separating light source 401 from sample 101.

Preferably sources 701 are partially surrounded by a concentrator 705. Concentrator 705 uses a combination of reflective surfaces, absorbing surfaces, and blocking surfaces in accordance with well known design techniques to provide the desired amount of additional light on portions 703. The amount of desired additional light is a function of both the sample/scanning bulb configuration and the sample/additional source configuration.

Figure 8:
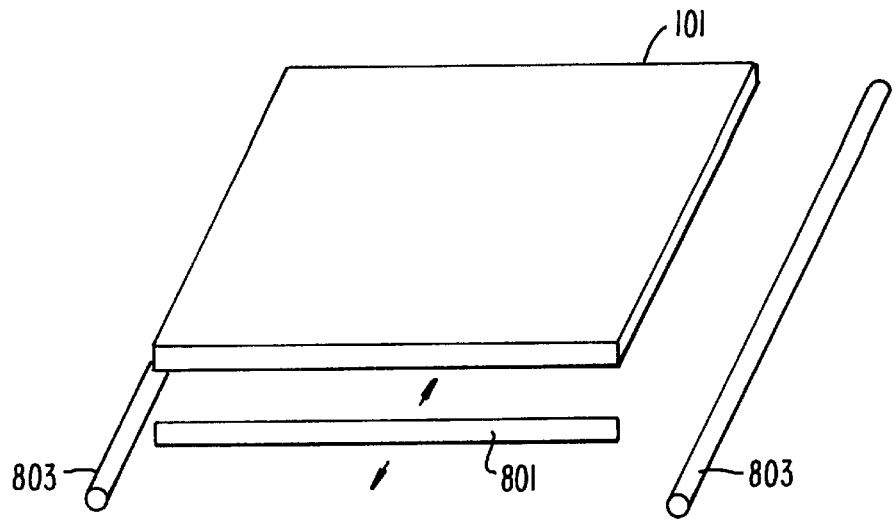
FIG. 8 is an illustration of an embodiment utilizing both stationary and scanning sources located on the same side of the sample under study.

FIG. 8 is an illustration of an alternate illumination configuration. As in the embodiment illustrated in FIG. 7, the illumination provided by a scanning source 801 is augmented by the illumination of one or more stationary sources 803. However in this embodiment both sources 803 and source 801 are located on the same side of sample 101. Preferably the detector is located on the opposite side of sample 101. Stationary sources 803 and scanning source 801 are optimized to insure uniform illumination of sample 101.

Figure 9:
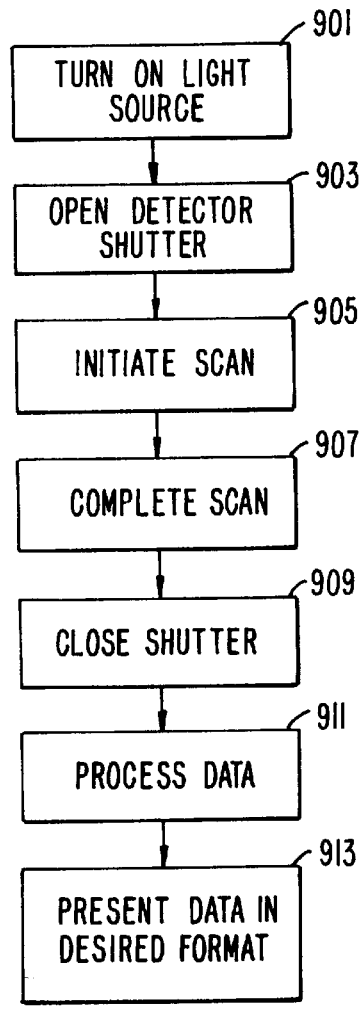
FIG. 9 is a block diagram outlining the principal steps associated with the scanning technique of the present invention.

FIG. 9 is a block diagram outlining the principal steps associated with the scanning technique of the present invention. To begin characterizing a sample, power is first supplied to the light source (step 901). Next, the shutter to the detector is opened (step 903). Although the shutter may be opened prior to turning on the light source, turning on the light source first allows stabilization to occur in the output of the source, thus minimizing uniformity fluctuations due to output variations. Once the shutter has been opened, the scan is initiated (step 905). The scan rate depends upon the desired illumination intensity as well as the output characteristics of the source. In the preferred embodiment, a scan rate of 25 centimeters per second is used. After the scan has been completed (step 907), the shutter is closed (step 909). At this point the data can be processed (step 911) and presented to the user (step 913). The presentation of the final data depends upon the type of detector, for example photocamera versus digital camera, as well as the desired output format (e.g., photograph, graph, table, color coded by intensity or emission wavelength, etc.).

As will be understood by those familiar with the art, the present invention may be embodied in other specific forms without departing from the spirit or essential characteristics thereof. For example, the number of bulbs and the exact dimensions of the bulbs can be varied depending upon the dimensions of the electrophoresis apparatus, the desired scan rate, and the uniformity requirements. Furthermore, the invention is equally applicable regardless of the bulb wavelengths. Accordingly, the disclosures and descriptions herein are intended to be illustrative, but not limiting, of the scope of the invention which is set forth in the following claims.

We claim:

1. An electrophoretic system comprising:

a stage for holding an electrophoresis gel, said gel containing at least one labeled region;

a scanning light source comprised of a plurality of light bulbs for irradiating said electrophoresis gel with radiation within at least a first wavelength band, said first wavelength band selected to excite said labeled region, wherein said excited labeled region fluoresces and emits radiation of at least a second wavelength;

a plurality of filters associated with said plurality of light bulbs; and a stationary detector for monitoring said radiation emitted by said labeled region, said stationary detector generating an output signal proportional to an intensity associated with said emitted radiation.

2. The electrophoretic system of claim 1, wherein said plurality of filters are selected from the group consisting of diffusing filters, absorbing filters, partially reflecting filters, and interference filters.

3. The electrophoretic system of claim 1, wherein said plurality of light bulbs have different output characteristics.

4. The electrophoretic system of claim 1, wherein said plurality of filters are interposed between said plurality of light bulbs and said electrophoresis gel.

5. An electrophoretic system, comprising:

a stage for holding an electrophoresis gel, said gel containing at least one labeled region, wherein said electrophoresis gel has a first dimension and a second dimension;

a scanning light source for irradiating said electrophoresis gel with radiation within at least a first wavelength band, said first wavelength band selected to excite said labeled region, wherein said excited labeled region fluoresces and emits radiation of at least a second wavelength, wherein said light source has an axis and a corresponding axis length, said axis parallel to said first dimension, and wherein said axis length is larger than said first dimension; and a stationary detector for monitoring said radiation emitted by said labeled region, said stationary detector generating an output signal proportional to an intensity associated with said emitted radiation.

6. An electrophoretic system, comprising:

a stage for holding an electrophoresis gel, said gel containing at least one labeled region;

a scanning light source for irradiating said electrophoresis gel with radiation within at least a first wavelength band, said first wavelength band selected to excite said labeled region, wherein said excited labeled region fluoresces and emits radiation of at least a second wavelength, wherein said scanning light source is located on a first side of said electrophoresis gel; and a stationary detector for monitoring said radiation emitted by said labeled region, said stationary detector generating an output signal proportional to an intensity associated with said emitted radiation, wherein said stationary detector is located on a second side of said electrophoresis gel.

7. A method of analyzing an electrophoresis gel, comprising the steps of:

opening a shutter to a stationary detector;

scanning the gel with radiation from a light source, wherein said scanned radiation is of a first wavelength band, said first wavelength band exciting at least one label corresponding to at least one labeled region within said electrophoresis gel, wherein said excited label fluoresces in a second wavelength band;

filtering said light source with a filter, wherein said filter is selected from the group consisting of diffusing filters, absorbing filters, partially reflecting filters, and interference filters; and detecting said fluorescence within said second wavelength band with said stationary detector, said stationary detector generating an output signal proportional to an intensity of said detected fluorescence.

8. A method of analyzing an electrophoresis gel, comprising the steps of:

opening a shutter to a stationary detector;

scanning the gel with radiation from a light source, wherein said scanned radiation is of a first wavelength band, said first wavelength band exciting at least one label corresponding to at least one labeled region within said electrophoresis gel, wherein said excited label emits radiation in a second wavelength band;

filtering said emitted radiation prior to detecting said emitted radiation, said filtering step removing substantially all of said radiation of said first wavelength band; and imaging said emitted radiation onto a stationary detector, wherein said stationary detector generates an output signal proportional to an intensity of said detected emitted radiation.

9. An electrophoretic system comprising:

a stage for holding an electrophoresis gel, said gel containing at least one labeled region;

a scanning light source for irradiating said electrophoresis gel with radiation within at least a first wavelength band, said first wavelength band selected to excite said labeled region, wherein said excited labeled region fluoresces and emits radiation of at least a second wavelength, wherein said scanning light is comprised of a plurality of light bulbs having different output characteristics; and a detector for monitoring said radiation emitted by said labeled region, said detector generating an output signal proportional to an intensity associated with said emitted radiation.

10. An electrophoretic system comprising:

a stage for holding an electrophoresis gel, said gel containing at least one labeled region;

a scanning light source for irradiating said electrophoresis gel with radiation within at least a first wavelength band, said first wavelength band selected to excite said labeled region, wherein said excited labeled region fluoresces and emits radiation of at least a second wavelength;

at least one stationary light source irradiating said electrophoresis gel with radiation of at least said first wavelength band, wherein said scanning light source and said stationary light source are co-located on a first side of said electrophoresis gel; and a detector for monitoring said radiation emitted by said labeled region, said detector generating an output signal proportional to an intensity associated with said emitted radiation.

11. An electrophoretic system comprising:

a stage for holding an electrophoresis gel, said gel containing at least one labeled region;

a scanning light source for irradiating said electrophoresis gel with radiation within at least a first wavelength band, said first wavelength band selected to excite said labeled region, wherein said excited labeled region fluoresces and emits radiation of at least a second wavelength;

at least one stationary light source irradiating said electrophoresis gel with radiation of at least said first wavelength band, wherein said scanning light source is located on a first side of said electrophoresis gel and said stationary light source is located on a second side of said electrophoresis gel; and a detector for monitoring said radiation emitted by said labeled region, said detector generating an output signal proportional to an intensity associated with said emitted radiation.

12. A method of analyzing an electrophoresis gel comprising the steps of:

opening a shutter to a detector;

scanning the gel with radiation from a light source, wherein said light source is comprised of a plurality of light bulbs, wherein said scanned radiation is of a first wavelength band, said first wavelength band exciting at least one label corresponding to at least one labeled region within said electrophoresis gel, wherein said excited label fluoresces in a second wavelength band;

individually controlling the output characteristics of each of said plurality of light bulbs; and detecting said fluorescence within said second wavelength band with said detector, said detector generating an output signal proportional to an intensity of said detected fluorescence.

13. A method of analyzing an electrophoresis gel comprising the steps of:

opening a shutter to a detector;

scanning the gel with radiation from a light source, wherein said scanned radiation is of a first wavelength band, said first wavelength band exciting at least one label corresponding to at least one labeled region within said electrophoresis gel, wherein said excited label fluoresces in a second wavelength band;

illuminating said electrophoresis gel with at least one stationary light source emitting radiation within said first wavelength band; and detecting said fluorescence within said second wavelength band with said detector, said detector generating an output signal proportional to an intensity of said detected fluorescence.

* * * * *